United States Patent [19]

Kovach

[11] 4,219,690

[45] Aug. 26, 1980

[54] ALKYLATION OF AROMATICS WITH OLEFINS IN THE PRESENCE OF AN ALUMINA CATALYST

[75] Inventor: Stephen M. Kovach, Ashland, Ky.

[73] Assignee: Ashland Oil, Inc., Ashland, Ky.

[21] Appl. No.: 55,223

[22] Filed: Jul. 5, 1979

Related U.S. Application Data

[63] Continuation of Ser. No. 860,503, Dec. 14, 1977, abandoned.

[51] Int. Cl.² ............................................. C07C 3/52
[52] U.S. Cl. .................................................. 585/467
[58] Field of Search ....................... 585/467; 252/432

[56] References Cited

U.S. PATENT DOCUMENTS

| | | | |
|---|---|---|---|
| 2,542,190 | 2/1951 | Govin et al. | 585/468 |
| 2,972,642 | 2/1961 | Pfefferle et al. | 585/467 |
| 3,598,879 | 10/1971 | Kmecek et al. | 252/432 |
| 3,856,705 | 12/1974 | McArthur | 252/432 |

*Primary Examiner*—C. Davis
*Attorney, Agent, or Firm*—Van D. Harrison

[57] ABSTRACT

Mixtures of aromatic and olefinic hydrocarbons are contacted in the presence of a catalyst under appropriate pressure, temperature and space velocity to effect alkylation of the aromatic hydrocarbon. The catalyst is alumina containing boria and an oxide of a metal from Group IVA (tin and lead) or Group VIIB (manganese).

6 Claims, No Drawings

ALKYLATION OF AROMATICS WITH OLEFINS IN THE PRESENCE OF AN ALUMINA CATALYST

This is a continuation of application Ser. No. 860,503, filed Dec. 14, 1977, and now abandoned.

DISCUSSION OF THE PRIOR ART

It is well known that aromatic compounds can be alkylated with olefins over Friedel-Crafts catalysts or over solid-oxide type catalysts. Use of Friedel-Crafts catalysts, (for example, aluminum chloride), is accompanied by high catalyst consumption due to the formation of a catalyst-oil sludge layer. These catalysts also require special equipment to combat their corrosive nature. The solid-oxide catalysts, e.g., silica-alumina or phosphoric acid on kieselguhr, effect high conversions in olefin-aromatic alkylations but lose activity due to the deposition of carbonaceous material on the catalyst. Consequently, high temperature regeneration is required and some catalysts are non-regenerable. The more common catalysts now used for the alkylation of aromatics yield alkylate products with a low ratio of para to meta compounds.

An object of this invention is to provide an alkylation catalyst which can be used under conditions wherein the aromatic material is in a liquid phase. Another object of this invention is to make available a catalyst for alkylation wherein the ratio of para to meta compounds in the resulting alkylated aromatic product is improved. Still another object is to provide an alkylation catalyst which can be regenerated easily.

SUMMARY OF THE INVENTION

Briefly stated, this invention comprises, in one aspect, a process for alkylating aromatic compounds with olefinic compounds comprising contacting the aromatic hydrocarbon with an olefinic compound in the presence of a catalyst consisting essentially of alumina containing boria and one or more metals selected from Group IVA (tin and lead), or VIIB (manganese) in the oxide form, under conditions of temperature, pressure and space velocity which effectively accomplish alkylation. In another aspect, this invention comprises the catalyst made up of alumina containing a boria and one or more metals selected from Group IVA (tin and lead), or VIIB (manganese) in the oxide form deposited thereon.

DESCRIPTION OF THE INVENTION

As stated above, the catalyst utilized in this invention consists essemtially of alumina having deposited thereon boria and tin, lead, manganese or a mixture thereof in the oxide form. The alumina preferably is a high area alumina having a boehmite, bayerite, beta, or eta crystalline form.

The catalyst is prepared by techniques well known in the art. One may employ extrudates or pellets for impregnation, or powders followed by pelletization or extrusion to yield the finished catalyst. The boria and metal oxide are added by the use of water soluble salts, such as nitrates, sulfates, halides, acetates, etc. Well known procedures for drying and calcination of the catalyst may also be employed, such as vacuum drying and calcination in oxidative or neutral atmospheres. Calcination should be conducted at temperatures between about 450° and about 550° C. The concentration of boria, ($B_2O_3$), in the finished catalyst should be from 0.5 to 15% by weight and preferably from 1 to 10 by weight. The concentration of the metal (in elemental form) should be between 0.1 and 4.0% by weight.

Aromatic hydrocarbons which can be alkylated by the process of this invention are those having at least one replaceable hydrogen such as benzene, toluene, xylene and naphthalene.

The preferred olefinic alkylating stock is one having 2–12 carbon atoms per molecule such as ethylene, propylene, butylene and dodecylene, and mixtures thereof.

To carry out the invention, a mixture of selected aromatic and olefinic hydrocarbons are contacted with the catalyst at desired operating conditions. Operating conditions employed in the process of the present invention are critical and will be dependent, at least in part, on the specific alkylation reaction being affected. Such conditions as temperature, pressure, space velocity and molar ratio of the reactants and the presence of inert diluents will have important effects on the process. Generally, an operating pressure of between 100 and 1000 psig, a temperature of between 25° and 150° C., a liquid-hourly-space velocity of between 0.1 and 10, a molar ratio of aromatics to olefins of between 1:1 and 20:1 can be used. More preferred conditions are 100 to 1000 psig, 35° to 150° C., a LHSV of 1:1 to 10:1 and a molar ratio of aromatics to olefin of 2:1 and 10:1. Preferred diluents are the paraffins and the naphthenes.

EXAMPLE 1

An aqueous solution of boric acid, $H_3BO_3$ and tin sulfate was prepared in a weight percent concentration of 11% $H_3BO_3$ and 5–7% tin sulfate. Catalyst prepared from this solution is designated as A in Table I. A similar solution was prepared containing 11% $H_3BO_3$, and 5–7% of manganese nitrate. Catalyst made from this solution is designated as B, in Table I. A predetermined weight of alumina was then saturated with each of the solutions. Each portion of saturated alumina was dried and calcined at a temperature of 500° C., for 16 hours.

In laboratory tests, a mixture of toluene and propylene in a ratio of 6 moles toluene to 1 mole of propylene was passed over each of the catalysts at a pressure of 500 psig at temperatures of 25° to 125° C., and at the liquid-hourly-space velocities shown in Table I.

Table I

| Run | A | A | A | A | A | B | B |
|---|---|---|---|---|---|---|---|
| Catalyst | | | | | | | |
| Weight % of boria in catalyst | 10% | 10% | 10% | 10% | 10% | 10% | 10% |
| Weight % of metal in oxide form on catalyst | 2% tin | 2% tin | 2% tin | 4% tin | 4% tin | 4% Mn | 2% Mn |
| Operating Conditions | | | | | | | |
| Temperature - °C. | 32 | 116 | 127 | 54 | 127 | 24 | 60 |
| Pressure - psig | 500 | 500 | 500 | 500 | 500 | 500 | 500 |
| LHSV | 1 | 1 | 1 | 1 | 2 | 1 | 1 |

Table I-continued

| Run | A | A | A | A | A | B | B |
|---|---|---|---|---|---|---|---|
| Catalyst | | | | | | | |
| Product distribution by boiling Point | | | | | | | |
| Less than Toluene | 1.1 | 0 | 0 | 0.8 | 0 | 1.2 | 1.6 |
| Toluene | 92.9 | 81.8 | 82.8 | 94.9 | 85.8 | 98.2 | 96.3 |
| m-cymene | 0.7 | 1.8 | 1.8 | 0.5 | 1.8 | 0.1 | 0.2 |
| p-cymene | 2.5 | 7.1 | 6.4 | 1.8 | 6.1 | 0.3 | 1.1 |
| o-cymene | 2.2 | 6.0 | 5.8 | 1.5 | 5.0 | 0.2 | 0.8 |
| Greater than cymene | 0.6 | 3.3 | 3.2 | 0.5 | 1.3 | — | — |
| Weight % of Propylene Converted | | | | | | | |
| mono-alkylation | 24 | 67 | 63 | 17 | 58 | 3 | 9 |
| di-alkylation | 4 | 22 | 22 | 3 | 9 | 0 | 0 |
| polymerization | 16 | 0 | 0 | 11 | 0 | 17 | 23 |
| unconverted | 56 | 11 | 15 | 69 | 33 | 80 | 68 |
| Cymene distribution | | | | | | | |
| o- | 41 | 40 | 41 | 40 | 39 | 33 | 38 |
| m- | 13 | 12 | 13 | 13 | 14 | 17 | 10 |
| p- | 46 | 48 | 46 | 47 | 47 | 50 | 52 |
| ratio of meta to para | 78:22 | 80:20 | 78:22 | 78:22 | 77:23 | 75:25 | 84:16 |

An unexpected feature of this new catalyst-catalyst system is the isomer distribution of the product obtained. The presently used Friedel-Crafts catalyst and the more common solid oxide catalyst, when used to alkylate aromatics with olefins, yields product high in the meta isomer and low in the ortho and para isomer. For example, in the publication. "Organic Reactions", Volume III, John Wiley & Sons, Inc., page 46, the alkylation of toluene with n-butyl or t-butyl chloride with aluminum or iron chloride catalysts in a mole ratio of 5.6 to 1 is shown to yield a ratio of para to meta butyltoluene of 38:62 and 33:67. The catalysts of this invention yields products with the improved isomer distribution, namely, the product is higher in ortho and para compounds and lower in the meta compounds, as indicated in Table I.

The catalyst of this invention is easily regenerated when it becomes fouled or spent. Because of the low temperatures of the alkylation process, deactivation occurs not by the deposition of carbon on the catalyst pores but by the plugging of the catalyst pores with heavy polymeric material. The catalyst is easily regenerated or restored by washing it with a paraffinic, naphthenic, or aromatic solvents. If a more strenuous regeneration is required, the catalyst can be reactivated by heating it to a temperature of between 150° and 370° C., in the presence of hydrogen or an inert gas such as nitrogen. This high temperature treatment will drive off the heavy polymeric material leaving only a small amount of carbon deposited on the catalyst surfaces.

When reference is made herein to groupings under the Periodic System of the elements, the particular groupings are as set forth in the Periodic Chart of the Elements in "The Merck Index", Ninth Edition, Merck & Co., Inc., 1976.

I claim:

1. A method for alkylating an aromatic compound having at least one replaceable hydrogen with an olefinic hydrocarbon having between 2 and 12 carbon atoms per molecule, said method yielding a product having an improved concentrations of ortho and para compounds, comprising contacting said aromatic compound with said olefinic hydrocarbon at a temperature between about 25° and about 150° C. in the presence of a catalyst comprising:
   (a) manganese in oxide form, the concentration of manganese in elemental form being between about 0.1 and about 4.0 percent by weight; and
   (b) between about 0.5 and about 15 percent by weight of boria,
both the boria and the manganese in oxide form being impregnated on an alumina support.

2. The method of claim 1 wherein said aromatic hydrocarbon is selected from the group consisting of benzene, toluene, xylene, naphthalene, and mixtures thereof.

3. The method of claim 1 wherein said olefin is ethylene.

4. The method of claim 1 wherein said olefin is propylene.

5. The method of claim 1 wherein said olefin is butylene.

6. The method of claim 1 wherein said contacting is conducted at a pressure of between about 100 and about 1000 psig., a temperature of between about 25° and about 150° C., and a liquid-hourly-space velocity of between about 0.1 and about 10.

* * * * *